US006239323B1

(12) United States Patent
Lieske et al.

(10) Patent No.: US 6,239,323 B1
(45) Date of Patent: May 29, 2001

(54) CATALYSER FOR AROMATISING ALIPHATIC AND ALICYCLIC HYDROCARBONS, METHODS OF PRODUCING AND USING SAID CATALYST

(75) Inventors: Heiner Lieske; Dang Lanh Hoang, both of Berlin (DE)

(73) Assignee: Institut für Angewandte Chemie Berlin-Adlershof e.V., Berlin (DE)

( * ) Notice: Subject to any disclaimer, the term of this patent is extended or adjusted under 35 U.S.C. 154(b) by 0 days.

(21) Appl. No.: 09/142,726

(22) PCT Filed: Mar. 18, 1997

(86) PCT No.: PCT/DE97/00616

§ 371 Date: Sep. 14, 1998

§ 102(e) Date: Sep. 14, 1998

(87) PCT Pub. No.: WO97/34691

PCT Pub. Date: Sep. 25, 1997

(30) Foreign Application Priority Data

Mar. 18, 1996 (DE) .............................. 196 12 000

(51) Int. Cl.$^7$ .................................................. C07C 15/00
(52) U.S. Cl. .................. 585/407; 502/305; 502/306; 502/319; 502/321; 502/324; 502/353
(58) Field of Search ..................... 502/305, 319, 502/321, 306, 324, 353, 300; 585/407

(56) References Cited

U.S. PATENT DOCUMENTS

| 3,884,834 | | 5/1975 | Eberly et al. . | |
|---|---|---|---|---|
| 3,981,794 | * | 9/1976 | Eberly | 208/138 |
| 4,176,089 | | 11/1979 | Cull . | |
| 4,233,139 | * | 11/1980 | Murrell et al. . | |
| 4,269,737 | * | 5/1981 | Grenoble et al. . | |
| 4,440,631 | * | 4/1984 | Togari et al. | 502/302 |
| 4,929,585 | * | 5/1990 | Lee et al. | 502/306 |
| 5,162,283 | | 11/1992 | Moini . | |

FOREIGN PATENT DOCUMENTS

| 19516318A1 | 4/1995 | (DE) . |
|---|---|---|
| 0527634A1 | 2/1993 | (EP) . |
| 0641597A1 | 3/1995 | (EP) . |

* cited by examiner

Primary Examiner—Tom Dunn
(74) Attorney, Agent, or Firm—Collard & Roe, P.C.

(57) ABSTRACT

The invention relates to a selective catalyst for aromatising hydrocarbons with at least 7 carbon atoms in the chain and to a method of manufacturing the catalyst. The catalyst is characterized by a porous oxide or mixture of oxides of one or more of the elements Ti, Zr and Hf containing in addition, at least at the surface, elements of sub-group V, VI and VII elements in oxidised form in quantities of 0.01 to 10 wt % of the total catalyst weight. The catalyst has a specific surface area of between 30 and 200 m$^2$/g and can repeatedly absorb and release hydrogen in the temperature range 400–700 ° C. It has no strongly acidic or strongly basic centers and can in addition contain compounds of group II or sub-group III elements including the lanthanides, as well as compounds of silicon and aluminium and mixtures thereof.

20 Claims, No Drawings

CATALYSER FOR AROMATISING ALIPHATIC AND ALICYCLIC HYDROCARBONS, METHODS OF PRODUCING AND USING SAID CATALYST

BACKGROUND OF THE INVENTION

1. Field of the Invention

The invention relates to a selective catalyst for aromatising aliphatic or alicyclic hydrocarbons with at least 7 carbon atoms in the chain, and to methods of its production and use.

2. The Prior Art

Aromatic compounds such as toluene, ethylbenzene, p-xylene and o-xylene are important aromatic hydrocarbons, which are components of high octane fuels and are used as starting materials for a wide variety of synthetic reactions in the chemical industry. Aromatisation thus belongs to the most important processes of petroleum chemistry for the refining of paraffinic hydrocarbons. Because of the indispensability of catalysts for the technical realisation of the aromatisation process, the development of effective catalysts is a constant demand on catalysis research.

The recovery of aromatic compounds from reactions of hydrocarbon fractions containing mainly $C_6$–$C_8$ paraffins has been carried out for decades according to the known reforming process and its modifications. The successfully used Pt/$Al_2O_3$ reforming catalysts, which have meanwhile been modified and improved in many ways, e.g. by the use of bi- or multi-metal additives and by variations of the substrate in different ways, are described for example by B. C. Gates, J. R. Kratzer and G. C. Schuit, Chemistry of Catalytic Processes, McGraw-Hill, N.Y. 1979. In general, a yield of 25–40% $C_6$–$C_8$ aromatic compounds is achieved at 450–550° C. and pressures of 1–2 MPa using a hydrogen/carbon molar ratio of 10/1 to 100/1 with catalysts containing 0.5–1.0% by weight of platinum. Side products of the reforming process are hydrogen formed by dehydrogenation reactions and lower paraffins formed by hydrogenolysis (hydrocracking), which reduce the yield of useful materials.

In spite of the progress achieved, the above named catalyst systems have disadvantages. Catalysts containing noble metals are expensive. The temporal stability of the catalysts under the necessary working conditions is worthy of improvement, meaning that additional expense and/or environmental problems occur in the regeneration or processing of the catalysts. The selectivity for the end-product is diminished by the above named side-reactions; the valuable crude oil carbon carrier is exploited inefficiently.

SUMMARY OF THE INVENTION

The object of the invention is to provide new catalysts with higher selectivity for aromatisation reactions, as well as providing methods for their production and their use in a catalytic aromatisation process.

According to the invention, this object is achieved with a selective aromatisation catalyst, characterised by a porous oxide or mixture of oxides of one or more of the elements Ti, Zr and Hf which, at least at the surface, additionally contains one or more of the elements of the 5th, 6th and 7th sub-group of the periodic system of the elements (PSE) in oxidised form, in amounts from 0.01 to 10% by weight relative to the total mass of the catalyst;

wherein said catalyst has a specific surface area in the range from 30 to 300 $m^2$/g;

has the ability to repeatedly absorb and release hydrogen in the temperature range from 400 to 700° C.;

and exhibits no strongly acidic and/or strongly basic centres.

The new catalysts may additionally contain an oxide or several oxides chosen from the elements of main group II, the elements of sub-group III including the lanthanides, the element silicon, the element aluminium and mixtures thereof in an amount ranging from 0.01 to 20% by weight relative to the total mass of the catalyst. Lanthanum, magnesium and calcium are particularly prefer- red.

Among the elements of the 5th, 6th and 7th sub-group those chosen from chromium, tungsten, molybdenum, niobium and tantalum are preferred, particularly Cr, W and Mo.

The catalyst may contain the oxidised form of the elements of the 5th, 6th and 7th sub-group at the surface of the porous structure; it may also contain them at the surface or within the body (in the bulk) of the catalyst.

The specific surface area, determined according to the BET method [(J. Amer. Chem. Soc. 60 (1938) 309], amounts to between 30 and 300 $m^2$/g, in particular 50 to 200 $m^2$/g.

The catalysts according to the invention prevalently exhibit no strongly acidic or strongly basic centres on their surface. Among others, this was determined by acidity and basicity measurements by means of temperature programmed desorption of ammonia (TPDA) or carbon dioxide (TPDCO$_2$).

With regard to the invention, suitable compounds are for example chlorides, oxychlorides, nitrates, alkylates and alcoholates as far as these exist for the individual elements.

The ability of the catalyst to repeatedly absorb hydrogen and—during a later rinsing with an inert gas—to completely release hydrogen is an essential feature of the invention. "Repeatedly absorb" and "completely release" means that after initial saturation with hydrogen and subsequent rinsing with inert gas, a catalyst essentially releases completely the subsequent amount of newly added hydrogen again. This characteristic of the catalyst has not yet been explained in terms of its mechanism and its interrelation with catalytic activity; nevertheless, it is an important precondition for the effectiveness according to the invention.

The invention also relates to production of the aromatisation catalysts carried out such that i) a suitable compound of Ti, Zr or Hf or a mixture of several of these compounds is transferred from a solution into a suspension of a hydroxide, oxide or mixture thereof, and the solid components of the suspension are separated off, and the product is modified at the surface with a solution of one or more of the compounds of the elements of the 5th, 6th and 7th sub-group, and subsequently calcined at 300 to 750° C. in air or oxygen;

or ii) a solution of a suitable compound of the elements Ti, Zr or Hf or a mixture thereof together with a solution of one or more compounds of the elements of the 5th, 6th and 7th sub-group is transferred into a suspension of an oxide, hydroxide or mixture thereof, the solid components of the suspension are separated off, and the product is calcined at 300 to 750° C. in air or oxygen.

Preferably, the process is carried in such a way that i) first of all, a hydroxide, oxide, mixture of oxides or hydroxide/oxide mixture of the elements titanium, zirconium and hafnium is made up of suitable compounds of these elements familiar to persons skilled in the art, preferably salts, by preparation methods familiar to persons skilled in the art, preferably by the steps of precipitation, filtration and drying, and that ii) this hydroxide, oxide, mixture of oxides or hydroxide/oxide mixture is subsequently modified at the surface— cumulatively or alternatively—with the elements of the 5th, 6th and 7th sub-group of the PSE using suitable compounds and suitable impregnation techniques, and then calcined in air or in oxygen at temperatures between 300 and 750° C. so that as a result these elements are present in oxidised form.

In special embodiments, one or more elements of main group II and sub-group III of the periodic system, including the lanthanides as well as aluminium or silicon or mixtures of said elements, may be additionally introduced in step i) by the addition of suitable compounds of these elements at suitable points of the preparation process. In other embodiments, step ii) may be evaded by introducing suitable compounds of the elements of the elements of the 5th, 6th and 7th sub-group cumulatively or alternatively in step i), so that as a result these elements are present as oxides both in the bulk and at the surface of the catalyst.

After separation of the solid components from a suspension of hydroxides, oxides or mixtures thereof, annealing may be carried out in every variant of the method until conversion of hydroxides into oxides.

The result of the preparation steps i) and ii) is subjected to thermal treatment in air or oxygen in the range of temperatures from 300 to 750° C. during which a porous solid with a surface area from 30 to 300 $m^2/g$ is formed, and which after cooling down, if necessary immediately prior to the catalytic reaction, is treated with hydrogen or a gas containing hydrogen in a temperature range from 400 to 700° C. over a period of at least 5 minutes and up to several hours, in the process of which the solid absorbs hydrogen. The catalyst has the characteristic of releasing the absorbed hydrogen completely if, for example, an inert gas is passed through it at a sufficiently high temperature. Measurement of this characteristic, which is important for the object of the invention, is performed by so-called temperature programmed reduction (TPR) and by temperature programmed desorption of hydrogen (TPDH).

The catalysts according to the invention are suitable for the selective catalytic conversion of aliphatic or alicyclic hydrocarbons into aromatic compounds.

The object of the invention is thus also the use of the catalysts described above for selective catalytic conversion of aliphatic or alicyclic hydrocarbons with at least 7 carbon atoms in the longest chain into alkyl substituted benzenes. The catalyst is particularly suitable for the catalytic conversion of saturated or unsaturated hydrocarbons with 7 to 12 carbon atoms in the chain. Saturated hydrocarbons with at least 7 to 12, preferably 7 to 10 and particularly 7 to 8 carbon atoms in the longest chain are preferred. Thus, for example, n-heptane is converted into toluene and n-octane into o-xylene and ethylbenzene with high selectivity.

In comparison with a classical Pt/$Al_2O_3$ catalyst, an increase of the $C_6$–$C_8$ aromatic selectivity from 61 to 97% is achieved with this new class of aromatisation catalysts, for example in the conversion of n-octane into alkyl aromatic compounds using a catalyst containing $ZrO_2$/La/Cr in accordance with the invention. The aromatic fraction created with the catalyst according to the invention consisted of about 90% of o-xylene and ethylbenzene and of only about 1% of physiologically objectionable benzene. Using Pt/$Al_2O_3$, by contrast, only about 33.4% $C_8$ aromatic compounds were created, but about 30% benzene.

The new catalysts show outstanding selectivity in the conversion of n-alkanes into aromatic compounds. They are particularly cost effective because of their ease of production and the relatively inexpensive components.

A further advantage consists in that the creation of physiologically objectionable benzene is almost completely suppressed when the input products have 7 or more carbon atoms in the chain. Moreover, the yield of useful products is increased at the expense of side products occurring otherwise.

DETAILED DESCRIPTION OF PREFERRED EMBODIMENTS

The invention is to be explained in more detail hereinafter.

EXAMPLE 1

Production of a $CrO_x$/$La_2O_3$/$ZrO_2$ Catalyst According to the Invention

A solution of 24.85 g $ZrOCl_2 \times 8H_2O$ and 1.33 g La($NO_3$)$_3 \times 6H_2O$ is prepared by introducing the salts slowly and with stirring into 50 ml of bi-distilled water at room temperature. The solution is added drop by drop and at the same time as a 25% $NH_3$ solution into distilled water, the pH value of which has been adjusted to 10 by means of $NH_3$. The hydroxide mixture obtained this way is washed so many times with distilled water after filtration until Cl ions can no longer be detected using an $AgNO_3$ test. The (Zr, La) hydroxide mixture is then dried in air at 120° C. for 24 hours.

The catalyst precursor obtained is further treated as follows:

13 g of the catalyst precursor are added slowly and with stirring to 50 ml of an 0.02 M ($NH_4$)$_2CrO_4$ solution at room temperature. The water is evaporated from the mixture obtained under continuous stirring for one hour at 50° C. The product is dried for 24 hours at 120° C. and subsequently treated in air for 4 hours at 600° C.

The $CrO_x$/$La_2O_3$/$ZrO_2$ catalyst obtained contains 0.6% by weight of Cr and possesses a specific surface area of 98 $m^2/g$ according to BET.

EXAMPLE 2

Production of a $MoO_x$/$La_2O_3$/$ZrO_2$ Catalyst 13 g of the catalyst precursor of example 1 are added slowly and with stirring to 50 ml of an 0.02 M ($NH_4$)$_6Mo_7O_{24} \times 4H_2O$ solution at room temperature. The water is evaporated from the mixture obtained under continuous stirring for an hour at 50° C. The product is dried for 24 hours at 120° C. and subsequently treated in air for 4 hours at 600° C.

The $MoO_x$/$La_2O_3$/$ZrO_2$ catalyst obtained contains 1% by weight of Mo and possesses a specific surface area of 88 $m^2/g$ according to BET.

EXAMPLE 3

Production of a $WoO_x$/$La_2O_3$/$ZrO_2$ Catalyst 13 g of the catalyst precursor of example 1 are added slowly and with stirring to 50 ml of an 0.01 M $Na_2WO_4 \times 2H_2O$ solution at room temperature. The water is evaporated from the mixture obtained under continuous stirring for an hour at 50° C. The product is dried for 24 hours at 120° C. and subsequently treated in air for 4 hours at 600° C.

The $WO_x/La_2O_3/ZrO_2$ catalyst obtained contains 1% by weight of W and possesses a specific surface area of 80 m$^2$/g according to BET.

EXAMPLE 4
Characterisation of a $CrO_x/La_2O_3/ZrO$, Catalyst According to the Invention by Measurement of the Hydrogen Adsorption Capacity by Means of Temperature Programmed Reduction (TPR) and Temperature Programmed Desorption of Hydrogen (TPDH)

TPR and TPDH measurements were carried out in an equipment corresponding to that specified by Robertson et al. (J. Catal. 37 (1975) 424). 500 mg of the catalyst produced according to example 1 was thermally treated in a flow of argon for one hour at 300° C. After cooling down to room temperature the sample was heated up at a heating rate of 10 K/min to a final temperature of 750° C. in a flow of 5% hydrogen in argon for the purpose of initial hydrogen adsorbance. Subsequently, the sample was cooled down to room temperature in the $H_2/Ar$ flow. Subsequently, the $H_2/Ar$ flow was replaced once again by Ar and the sample linearly heated up at 10 K/min to 750° C. in the Ar flow in order to desorb the hydrogen taken up.

After this pre-treatment procedure, a linear heating up of the sample to 750° C. in the 5% hydrogen in argon flow was carried out once again. The consumption of hydrogen occurring was detected catharometrically and yielded the TRP result characterised by the hydrogen consumption and the peak maximum temperature shown in Table 1. After cooling down, linear heating up to 750° C. in the Ar flow was carried out.

The amount of hydrogen being desorbed was again recorded continuously and yielded the TPDH result in Table 1. The TPR and TPDH results are a measure of the reversible hydrogen adsorption or desorption capacity of the catalyst in the range of reaction temperatures of the catalytic reactions.

| TPR | | TPDH | |
|---|---|---|---|
| H$_2$ consumption in mmol/g$_{catalyst}$ | T$_{max}$, ° C. | H$_2$ desorption in mmol/g$_{catalyst}$ | T$_{max}$, ° C. |
| 0.0245 | approx. 490 | 0.0253 | approx. 550 |

EXAMPLE 5
Catalytic Testing of a Catalyst According to the Invention

The catalytic reaction was performed in a temperature regulated quartz column-flow reactor with a diameter of 8 mm heated by means of a radiation oven. A sample of 500 mg of the $CrO_x$—$La_2O_3/ZrO_2$ catalyst produced according to sample 1 with a grain size of 0.3 mm to 0.8 mm was treated in the reactor for one hour at 550° C. in flowing hydrogen. Subsequently, a flow of hydrogen saturated with n-octane as shown in Table 2 was passed over the catalyst at the same temperature. The reaction attained a stationary state after one hour. Analysis of the reaction products was carried out by online gas chromatography; the gas chromatographic separation of the aromatic compounds as well as the other $C_5$–$C_9$ hydrocarbons took place on a Benton-34 column, that of the low boiling $C_1$–$C_4$ reaction products on an aluminium oxide column.

Calculation of the degree of conversion U and the selectivity S took place according to:

$$U = (E-A) \times 100/E;$$

with

E: number of moles of hydrocarbons put in, and

U: number of moles of hydrocarbons which failed to react;

$$S = P_i \times n \times 100/(E-A) \times m;$$

with

P$_i$: number with of moles of the product i, n: number of carbon atoms in i, and m: number of carbon atoms in the educt.

TABLE 2
Results of the n-octane conversion via the $CrO_x/La_2O_3/ZrO_2$ catalyst at normal pressure after one hour reaction time, weight of catalyst 500 mg, reaction temperature 550° C., molar ratio of n-octane/H$_2$ = 1/12.5, hydrogen flow 3 l/h.

| | Selectivity in % of C | | |
|---|---|---|---|
| n-octane degree of conversion in % | C$_1$–C$_4$ alkanes | C$_2$–C$_4$ alkanes | C$_6$–C$_8$ aromatic compounds |
| 70.5 | 0.19 | 0.1 | 97 |

| Aromatic distribution, mole-% | | | | | | |
|---|---|---|---|---|---|---|
| benzene | toluene | p-xylene | m-xylene | o-xylene | ethylbenzene | styrene |
| 1 | 6.1 | 4.7 | 6.5 | 53.7 | 27.4 | 1.3 |

EXAMPLE 6
Catalytic Testing of a $MoO_x/La_2O_3/ZrO_2$ Catalyst Produced According to Example 2

The test was carried out analogously to example 5.

TABLE 3
Results of the n-octane conversion via the $MoO_x/La_2O_3/ZrO_2$ catalyst at normal pressure after one hour reaction time, weight of catalyst 500 mg, reaction temperature 550° C., molar ratio of n-octane/H$_2$ = 1/12.5, hydrogen flow 3 l/h.

| | Selectivity in % of C | | |
|---|---|---|---|
| n-octane degree of conversion in % | C$_1$–C$_4$ alkanes | C$_2$–C$_4$ alkanes | C$_6$–C$_8$ aromatic compounds |
| 40.2 | 0.38 | 0.05 | 94 |

| Aromatic distribution, mole-% | | | | | | |
|---|---|---|---|---|---|---|
| benzene | toluene | p-xylene | m-xylene | o-xylene | ethylbenzene | styrene |
| 1.7 | 7.1 | 4.1 | 4.9 | 56.9 | 24.7 | 1.1 |

EXAMPLE 7
Catalytic Testing of a $WoO_x/La_2O_3/ZrO_2$ Catalyst Produced According to Example 3

The test was carried out analogously to example 5.

TABLE 4

Results of the n-octane conversion via the $WO_x/La_2O_3/ZrO_2$ catalyst at normal pressure after one hour reaction time, weight of catalyst 500 mg, reaction temperature 550° C., molar ratio of n-octane/$H_2$ = 1/12.5, hydrogen flow 3 l/h.

| n-octane degree of conversion in % | Selectivity in % of C | | |
|---|---|---|---|
| | $C_1$–$C_4$ alkanes | $C_2$–$C_4$ alkanes | $C_6$–$C_8$ aromatic compounds |
| 21.2 | 1.5 | 2.4 | 80.3 |

| Aromatic distribution, mole-% | | | | | | |
|---|---|---|---|---|---|---|
| benzene | toluene | p-xylene | m-xylene | o-xylene | ethylbenzene | styrene |
| 1.1 | 1.4 | 3.7 | 5.7 | 60 | 27.7 | 0 |

EXAMPLE 8
Catalytic Testing of a Comparison Catalyst $Pt/Al_2O_3$

This comparison catalyst concerns a classical reforming catalyst produced by impregnation of a γ-$Al_2O_3$ with a specific surface area of 300 m²/g with hexachloroplatinic (IV) acid. The platinum content was 0.5% by weight. Subsequent to impregnation, the catalyst was calcined in air for one hour at 550° C. and then reduced for one hour in hydrogen. The catalytic testing was carried out analogously to example 5.

TABLE 5

Results of the n-octane conversion via the $Pt/Al_2O_3$ catalyst at normal pressure after one hour reaction time, weight of catalyst 500 mg, reaction temperature 450° C., molar ratio of n-octane/$H_2$ = 1/12.5, hydrogen flow 3 l/h.

| n-octane degree of conversion in % | Selectivity in % of C | | |
|---|---|---|---|
| | $C_1$–$C_4$ alkanes | $C_2$–$C_4$ alkanes | $C_6$–$C_8$ aromatic compounds |
| 90.2 | 37.6 | — | 61.0 |

| Aromatic distribution, mole-% | | | | | | |
|---|---|---|---|---|---|---|
| benzene | toluene | p-xylene | m-xylene | o-xylene | ethylbenzene | styrene |
| 30.1 | 34.0 | 4.1 | 16.6 | 11.3 | 1.4 | 0 |

EXAMPLE 9
Testing of a $CrO_x/ZrO_2$ Catalyst

A catalyst was produced by impregnation of a zirconium hydroxide sample supplied by Messrs. MEL with 0.02 M $(NH_4)CrO_4$ solution. The Cr content was 0.6%. Subsequent to impregnation, the catalyst was calcined in air for four hours at 600° C. and then reduced for one hour in hydrogen. After this pre-treatment the catalyst possesses a specific surface area of 44 m²/g according to BET. The catalytic testing was carried out analogously to example 5.

TABLE 7

Results of the n-octane conversion via the $CrO_x/ZrO_2$ catalyst at normal pressure after one hour reaction time, weight of catalyst 500 mg, reaction temperature 550° C., molar ratio of n-octane/$H_2$ = 1/12.5, hydrogen flow 3 l/h.

| n-octane degree of conversion in % | Selectivity in % of C | | |
|---|---|---|---|
| | $C_1$–$C_4$ alkanes | $C_2$–$C_4$ alkanes | $C_6$–$C_8$ aromatic compounds |
| 22.2 | 0.1 | 0.2 | 95.3 |

| Aromatic distribution, mole-% | | | | | | |
|---|---|---|---|---|---|---|
| benzene | toluene | p-xylene | m-xylene | o-xylene | ethylbenzene | styrene |
| 0.8 | 4.2 | 3.7 | 7 | 55.6 | 25.6 | 1.2 |

What is claimed is:

1. A catalyst for aromatizing aliphatic hydrocarbons and alicyclic hydrocarbons consisting of
   a porous oxide or mixture of oxides of at least one element selected from the group consisting of Zr and Hf containing in addition, at least at the surface, at least one element selected from the group consisting of Nb, Cr, W, Mn, Ta and Re in oxidized form in an amount of 0.01% to 10% by weight relative to the total weight of the catalyst;
   said catalyst having a specific surface area in the range of 30 to 300 m²/g; said catalyst having an ability to repeatedly absorb and[]desorb hydrogen in the temperature range from 400° C. to 700° C.; and
   said catalyst having no strongly acidic centers or no strongly basic centers or no strongly acidic centers and no strongly basic centers.

2. The catalyst according to claim 1, wherein the element present at least at the surface of the porous oxide or mixture of oxides, is selected from the group consisting of chromium, and tungsten.

3. The catalyst according to claim 1, wherein the element selected from the group consisting of, Nb, Cr, W, Mn, Ta and Re is present at the surface and in the bulk of the catalyst.

4. A catalyst for aromatizing aliphatic hydrocarbons and alicyclic hydrocarbons consisting of
   a porous oxide or mixture of oxides of at least one element selected from the group consisting of Zr and Hf containing in addition, at least at the surface, at least one element selected from the group consisting of Nb, Cr, W, Mn, Ta and Re in oxidized form in an amount of 0.01% to 10% by weight relative to the total weight of the catalyst;
   said catalyst having a specific surface area in the range of 30 to 300 m²/g; said catalyst having an ability to repeatedly absorb and desorb hydrogen in the temperature range from 400° C. to 700° C.; and
   said catalyst having no strongly acidic centers or no strongly basic centers or no strongly acidic centers and no strongly basic centers; and
   additionally containing an oxide or several oxides chosen from the elements of main group II, the elements of sub-group III including the lanthanides, the element silicon, the element aluminum and mixtures thereof in an amount from 0.01% to 20% by weight relative to the total weight of the catalyst.

5. A process for preparing a catalyst for aromatizing aliphatic hydrocarbons and alicyclic hydrocarbons consists of a procedure selected from the group consisting of
   (a) transferring a compound of Zr or Hf or a mixture thereof from a solution into a suspension of a hydroxide, oxide or mixture thereof, and separating off the solid components of the suspension; modifying the product at the surface with a solution of at least one compound of elements selected from the group consisting of Nb, Cr, W, Mn, Ta and Re, and subsequently calcining at 300° C. to 750° C. in air or oxygen; and
   (b) transferring a solution of a compound of the elements Zr or Hf or a mixture thereof together with a solution of at least one compound of elements selected from the group consisting of Nb, Cr, W, Mn, Ta and Re into a suspension of a hydroxide, oxide or mixture thereof; separating off the solid components of the suspension; and calcining the product at 300° C. to 7500C in air or oxygen.

6. The process according to claim 5, wherein the solid components separated from the suspension are annealed until the conversion of hydroxides into oxides prior to the addition of at least one compound of the elements selected from the group consisting of Nb, Cr, W, Mn, Ta and Re.

7. A process for preparing a catalyst for aromatizing aliphatic hydrocarbons and alicyclic hydrocarbons consisting of a procedure selected from the group consisting of
   (a) transferring a compound of Zr or Hf or a mixture thereof from a solution into a suspension of a hydroxide, oxide or mixture thereof, and separating off the solid components of the suspension; modifying the product at the surface with a solution of at least one compound of elements selected from the group consisting of Nb, Cr, W, Mn, Ta and Re, and subsequently calcining at 300° C. to 750° C. in air or oxygen; and
   (b) transferring a solution of a compound of the elements Zr or Hf or a mixture thereof together with a solution of at least one compound of elements selected from the group consisting of Nb, Cr, W, Mn, Ta and Re into a suspension of a hydroxide, oxide or mixture thereof; separating off the solid components of the suspension; and calcining the product at 300° C. to 750° C. in air or oxygen; and
   wherein additionally a compound or several compounds of elements chosen among the elements of main group II, the elements of sub-group III including the lanthanides, the element aluminum and mixtures thereof,
   (a) is added to the solution of the compound of Zr or Hf or mixtures thereof; or
   (b) is added to the solution of the compounds of the elements selected from the group consisting of Nb, Cr, W, Mn, Ta and Re; or
   (c) is added to the solution of the compound of Zr or Hf or mixtures thereof together with the solution of at least one compound of an element selected from the group consisting of Nb, Cr, W, Mn, Ta and Re and transferred into a suspension of hydroxide, oxide or mixture thereof, prior to the solid components of the suspension being filtered off, and prior to the product being calcined at 300° to 750° C. in air or oxygen.

8. A catalyst for aromatizing aliphatic hydrocarbons and alicyclic hydrocarbons consisting of
   a porous oxide or mixture of oxides of at least one element selected from the group consisting of Zr and La containing in addition, at least at the surface, at least one element selected from the group consisting of Cr, and W, in oxidized form in an amount of 0.01% to 10% by weight relative to the total weight of the catalyst;
   said catalyst having a specific surface area in the range of 30 to 300 $m^2/g$; said catalyst having an ability to repeatedly absorb and desorb hydrogen in the temperature range from 400° C. to 700° C.; and
   said catalyst exhibiting no strongly acidic centers or no strongly basic centers or no strongly acidic centers and no strongly basic centers.

9. The catalyst according to claim 8, which is selected from the group consisting of $CrO_x/La_2O_3/ZrO_2$, $WO_x/La_2O_3/ZrO_2$, and $CrOx/ZrO_2$.

10. The catalyst according to claim 9, which is $CrO_x/La_2O_3/ZrO_2$.

11. The catalyst according to claim 9, which is $WO_x/La_2O_3/ZrO_2$.

12. The catalyst according to claim 9, which is $CrO_x/ZrO_2$.

13. A process for preparing a catalyst for aromatizing aliphatic hydrocarbons and alicyclic hydrocarbons consisting of a procedure selected from the group consisting of
   (a) transferring a compound of Zr or La or a mixture thereof from a solution into a suspension of a hydroxide, oxide or mixture thereof, and separating off the solid components of the suspension; and modifying the product at the surface with a solution of one or more compounds of the elements selected from the group consisting of Cr, and W and subsequently calcining at 300° C. to 750° C. in air or oxygen; and
   (b) transferring a solution of a compound of the elements Zr or La or a mixture thereof together with a solution of one or more compounds of the elements selected from the group consisting of Cr, and W, into a suspension of a hydroxide, oxide or mixture thereof; separating off the solid components of the suspension; and calcining the product at 300° C. to 750° C. in air or oxygen.

14. A process for preparing a catalyst for aromatizing aliphatic hydrocarbons and alicyclic hydrocarbons consisting of a procedure selected from the group consisting of
   (a) transferring a compound of Zr or La or a mixture thereof from a solution into a suspension of a hydroxide, oxide or mixture thereof, and separating off the solid components of the suspension; and modifying the product at the surface with a solution of one or more compounds of the elements selected from the group consisting of Cr, and W and subsequently calcining at 300° C. to 750° C. in air or oxygen; and
   (b) transferring a solution of a compound of the elements Zr or La or a mixture thereof together with a solution of one or more compounds of the elements selected from the group consisting of Cr, and W, into a suspension of a hydroxide, oxide or mixture thereof; separating off the solid components of the suspension; and calcining the product at 300° C. to 750° C. in air or oxygen; and
   wherein additionally a compound or several compounds of elements chosen among the elements of main group II, the elements of sub-group III including the lanthanides, the element aluminum and mixtures thereof,
   (a) is added to the solution of the compound of Zr or La or mixtures thereof; or
   (b) is added to the solution of the compounds of the elements selected from the group consisting of Cr, and W; or (c) is added to the solution of the compound of Zr or La or mixtures thereof together with the solution of one or more compounds of the elements selected from the group consisting of Cr, and W, and transferred into a suspension of hydroxide, oxide or mixture thereof, prior to the solid components of the suspension being filtered off, and prior to the product being calcined at 300° C. to 750° C. in air or oxygen.

15. A method for the catalytic conversion of aliphatic hydrocarbons or alicyclic hydrocarbons with 7 to 12 carbon atoms in the longest chain or mixtures thereof into alkyl substituted benzenes having 7 to 12 carbon atoms comprising contacting said hydrocarbons with a catalyst for aromatizing aliphatic hydrocarbons and alicyclic hydrocarbons comprising a porous oxide or mixture of oxides of at least one element selected from the group consisting of Zr and Hf containing in addition, at least at the surface, at least one element selected from the group consisting of V, Nb, Cr, Mo, W, Mn, Ta and Re in oxidized form in an amount of 0.01% to 10% by weight relative to the total weight of the catalyst;

said catalyst having a specific surface area in the range of 30 to 300 $m^2/g$; said catalyst having an ability to repeatedly absorb and desorb hydrogen in the temperature range from 400° C. to 700° C.;

said catalyst having no strongly acidic centers or no strongly basic centers or no strongly acidic centers and no strongly basic centers; and producing an alkyl substituted benzene.

16. The method according to claim 15, wherein said aliphatic hydrocarbon is n-heptane; and wherein said alkyl substituted benzene is toluene.

17. The method according to claim 15, wherein said aliphatic hydrocarbon is n-octane and said alkyl substituted benzene is a mixture of o-xylene and ethylbenzene.

18. A method for the catalytic conversion of aliphatic hydrocarbons or alicyclic hydrocarbons with 7 to 12 carbon atoms in the longest chain or mixtures thereof into alkyl substituted benzenes having 7 to 12 carbon atoms comprising contacting said hydrocarbons with a catalyst for aromatizing aliphatic hydrocarbons and alicyclic hydrocarbons, comprising a porous oxide or mixture of oxides of at least one element selected from the group consisting of Zr and La containing in addition, at least at the surface, at least one element selected from the group consisting of Cr, Mo and W, in oxidized form in an amount of 0.01% to 10% by weight relative to the total weight of the catalyst;

said catalyst having a specific surface area in the range of 30 to 300 $m^2/g$; said catalyst having an ability to repeatedly absorb and desorb hydrogen in the temperature range from 400° C. to 700° C.;

said catalyst exhibiting no strongly acidic centers or no strongly basic centers or no strongly acidic centers and no strongly basic centers; and producing an alkyl substituted benzene.

19. The method according to claim 18, wherein the aliphatic hydrocarbon is n-heptane; and wherein the alkyl substituted benzene is toluene.

20. The method according to claim 18, wherein the aliphatic hydrocarbon is n-octane; and wherein the alkyl substituted benzene is a mixture of o-xylene and ethylbenzene.

* * * * *